(12) United States Patent
Lu et al.

(10) Patent No.: US 9,664,611 B2
(45) Date of Patent: May 30, 2017

(54) TESTING EQUIPMENT WITH MAGNIFYING FUNCTION

(71) Applicant: Bonraybio Co., Ltd., Taichung (TW)

(72) Inventors: Hui-Ching Lu, Taichung (TW); Cheng-Teng Hsu, Taichung (TW)

(73) Assignee: BONRAYBIO CO., LTD., Taichung (TW)

( * ) Notice: Subject to any disclaimer, the term of this patent is extended or adjusted under 35 U.S.C. 154(b) by 138 days.

(21) Appl. No.: 14/711,732

(22) Filed: May 13, 2015

(65) Prior Publication Data
US 2016/0131573 A1     May 12, 2016

(30) Foreign Application Priority Data

Nov. 7, 2014  (TW) .............................. 103138671 A
Mar. 30, 2015 (TW) .............................. 104110298 A

(51) Int. Cl.
G01N 21/03    (2006.01)
G01N 33/487   (2006.01)
G01N 21/80    (2006.01)

(52) U.S. Cl.
CPC ... *G01N 21/0303* (2013.01); *G01N 33/48778* (2013.01); *G01N 21/80* (2013.01); *G01N 2021/0389* (2013.01)

(58) Field of Classification Search
None
See application file for complete search history.

(56) References Cited

U.S. PATENT DOCUMENTS

| 3,656,840 A * | 4/1972 | Smith ................... G02B 27/06 359/804 |
| 5,267,087 A * | 11/1993 | Weidemann ....... A61B 10/0012 359/385 |
| 5,572,370 A * | 11/1996 | Cho ........................ G02B 25/02 359/379 |
| 2002/0044347 A1* | 4/2002 | Steenblik ........... G02B 21/0008 359/368 |
| 2002/0048819 A1 | 4/2002 | Alley |
| 2009/0251751 A1* | 10/2009 | Kuhlmann ......... G02B 27/1086 359/15 |

(Continued)

FOREIGN PATENT DOCUMENTS

| CN | 2269833 | 12/1997 |
| CN | 201535752 | 7/2010 |

(Continued)

OTHER PUBLICATIONS

"Search Report of PCT Counterpart Application", issued on Dec. 31, 2015, with partial English translation thereof, p. 1-p. 14.

*Primary Examiner* — Kara E Geisel
*Assistant Examiner* — Amanda Merlino
(74) *Attorney, Agent, or Firm* — Perkins Coie LLP; Viola T. Kung

(57) ABSTRACT

A testing equipment with a magnifying function includes a carrier, a cover and a magnifying part. The carrier has a specimen holding area formed on the top of the carrier. The cover is stacked on the specimen holding area of the carrier. The magnifying part disposed on the cover. The location of the magnifying part is corresponding to the location of the specimen holding area. The testing equipment of the present application has a simplified and cheap structure for a simple specimen testing.

13 Claims, 11 Drawing Sheets

(56) References Cited

U.S. PATENT DOCUMENTS

2013/0273524 A1   10/2013  Ehrenkranz et al.
2015/0276736 A1*  10/2015  Boilard .............. G01N 15/1459
                                                        435/6.1
2016/0004057 A1*   1/2016  Lin .................... G02B 21/0008
                                                        359/363

FOREIGN PATENT DOCUMENTS

| CN | 202083642 | 12/2011 |
| CN | 202974876 | 6/2013 |
| CN | 102236011 B | 10/2013 |
| CN | 203232198 | 10/2013 |
| CN | 203688559 | 7/2014 |
| TW | M491168 U | 12/2014 |
| TW | M491840 U | 12/2014 |

* cited by examiner

TESTING EQUIPMENT WITH MAGNIFYING FUNCTION

CROSS-REFERENCE TO RELATED APPLICATION

This application claims the priority benefits of Taiwan application serial no. 103138671, filed on Nov. 7, 2014 and Taiwan application serial no. 104110298, filed on Mar. 30, 2015. The entirety of each of the above-mentioned patent applications is hereby incorporated by reference herein and made a part of this specification.

BACKGROUND OF THE INVENTION

1. Field of the Invention

The invention relates to a testing equipment, and relates particularly to a testing equipment with a magnifying function.

2. Description of Related Art

Currently, testing of fluid state contents, are typically consigned to professional testing authorities for performing testing by high magnification, expensive microscope equipment. In the situation where an individual does not have microscope equipment, the testing activity cannot be performed by the individual.

However, in some testing categories nowadays testing is required to be performed on a regular basis; therefore generally for an individual it creates an excessive burden that consumes large amounts of time and money. For example, currently some medical procedures in the long term testing category are directed at infertility patients and include semen testing. This testing category is mainly directed at performing observations on the number of sperms, their motility and morphology. The method thereof mainly involves resting semen of a male subject at room temperature for a period of time, and taking a drop and instilling to a slide and setting under a microscope to perform observations for a period of time. The observations not only may be directed at performing high magnification observation of individual sperm to understand the external appearance of individual sperm, but may also be directed at performing observations of overall sperms in a group range, and their motility, morphology and the quantity per unit area. However, the reason why an individual is unable to perform testing is due to the reason that current related industries have not yet developed a testing product and the technology that conveniently allows an individual to perform testing through a simple aiding device. This problem is an important technical issue worthy to be considered and solved by related industries.

Of course, the testing category aforementioned is only one specific problem desired to be solved by the invention. Observational needs such as for medical specimens or motility, morphology of water micro-organisms, water quality, skin epidermis tissues/cells and which other individual want to understand, also necessitates the need for developing a simple testing product with significantly lower cost of use than current microscope equipment.

Directed at the aforementioned problems in conventional testing technology of specimen, how to develop a more ideal and practical innovative structure is a goal and a direction in which related industries need a breakthrough.

In view of this, the inventor's many years of experience of engagement in the manufacturing, development and design directed at the aforementioned goal, after detailed design and careful assessment has finally achieved a practical invention.

SUMMARY OF THE INVENTION

The invention provides a testing equipment with magnifying function, which solves a problem of past testing equipment being expensive, consuming high labor and not easy to popularize.

The invention provides a testing equipment with magnifying function, including a carrier, having at least one specimen holding area; a cover, at least stacked on the specimen holding area of the carrier; and at least one magnifying part, disposed at the cover, the magnifying part is disposed to align with the specimen holding area of the carrier.

In an embodiment of the invention, a number of the magnifying part is a plurality, disposed in intervals at the cover and with a magnification different to each other.

In an embodiment of the invention, the carrier further includes a light beam auxiliary guiding structure, such that a light beam from an outside environment is guided throughout the specimen holding area of the carrier.

In an embodiment of the invention, the testing equipment with magnifying function includes a non slip film, attached on top the cover, used to attach the cover to a camera of the intelligent communications device, so the magnifying part corresponds to the camera of the intelligent communications device.

Based on the above, the invention provides a simple structure for a testing equipment with a magnifying function in which the cost is significantly lowered, and is suitable for performing simple specimen magnification testing and is not only practical but has improvements.

Reference will now be made in detail to the present preferred embodiments of the invention, examples of which are illustrated in the accompanying drawings.

DESCRIPTION OF THE EMBODIMENTS

Figure 1A:
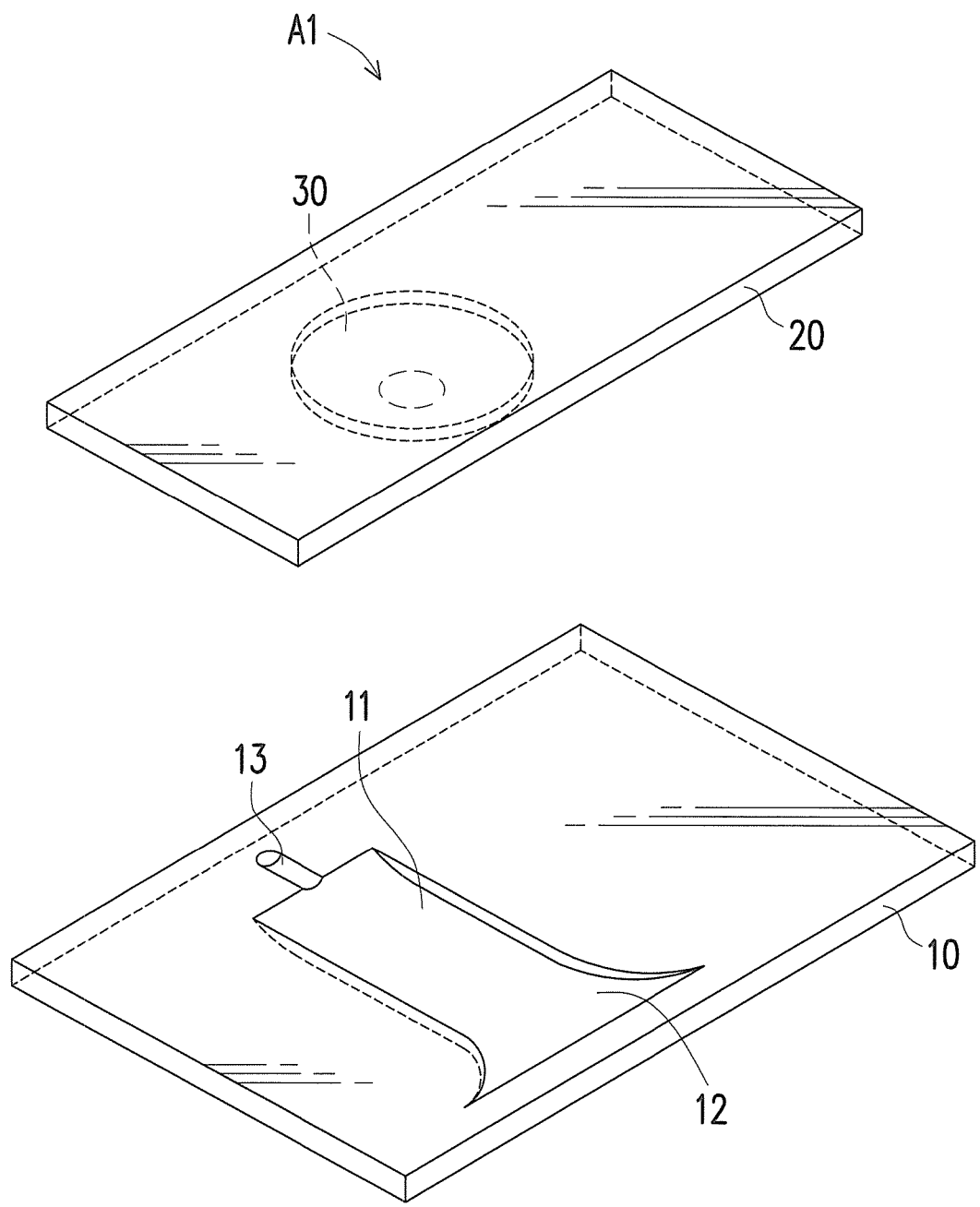
FIG. 1A is an exploded view of a testing equipment with magnifying function according to an embodiment of the invention.
Figure 1B:
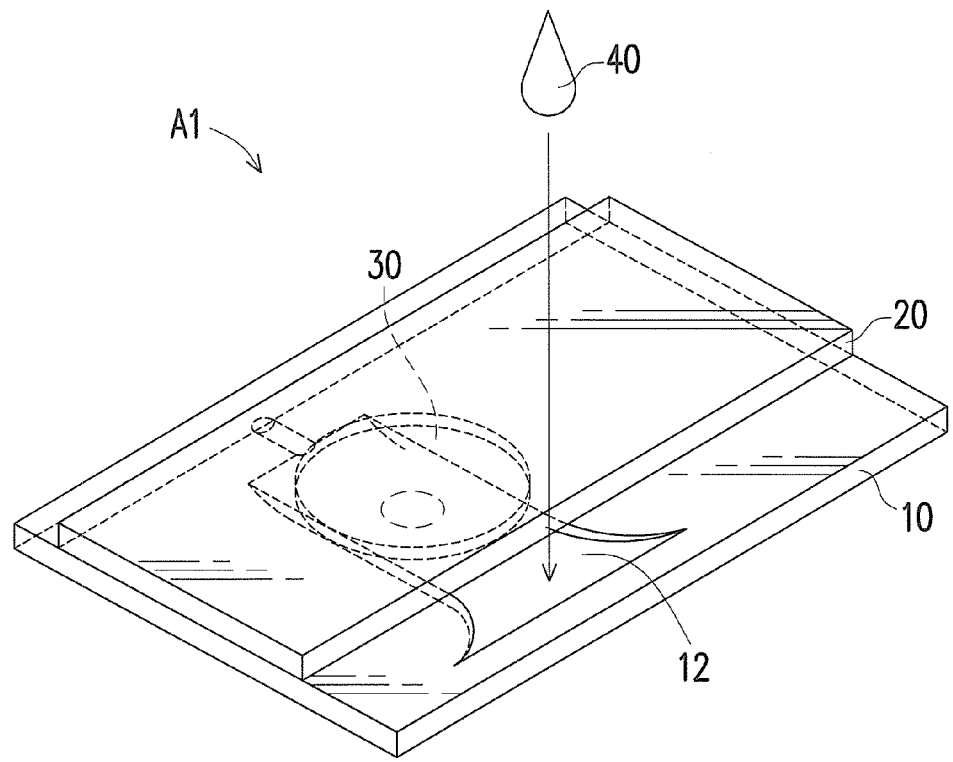
FIG. 1B is an assembled view of the testing equipment of FIG. 1A.

FIG. 1A and FIG. 1B is a testing equipment with magnifying function according to an embodiment of the invention. The embodiment is used for providing description and should not be construed as a limitation to the invention. The testing equipment with magnifying function A1 includes: a carrier 10 having a specimen holding area 11 formed on top, a cover 20 stacked on top of the carrier 10, and at least one magnifying part 30 rendering a convex lens type surface formed on the cover 20. The magnifying part 30 of the present embodiment uses a planar convex lens as an example; however a dual sided lenticular or other type of magnifying lens may be adopted. The magnifying part 30 is disposed to correspond with the specimen holding area 11 of the carrier 10. The magnification of the magnifying part 30 may have different magnifications according to testing requirements of different tests. The magnifying part 30 and the cover 20 may be integrally formed, namely the magnifying part 30 and the cover 20 is a single component. In other embodiments, the cover and the magnifying part may each be individual components that are adapted to be integrated together for conveniently integrating magnifying parts of different magnifications with the same cover. In other words, using the testing equipment A1 with magnifying function of the present embodiment does not require a magnifying lens or microscope and such tools to be additionally arranged for achieving a purpose of testing. Furthermore, an additional step for alignment is also not necessary and is highly convenient.

As shown in FIG. 1A, the specimen holding area 11 of the carrier 10 may specifically be formed with a depressed configuration. A more stable and larger storage space may be provided to a specimen 40 through the depressed configuration design, addressing the requirement where certain specimens are required to rest for a period of time before testing is performed. For example, before it is desired to perform the aforementioned motility testing on semen, it is necessary to be rested in room temperature for a period of time before testing is performed. Under these circumstances, the specimen 40 may be first instilled in the depressed configuration design specimen holding area 11 of the carrier 10 to rest for a period of time. As shown in FIG. 1B, an area of the cover 20 may be smaller than an area of the carrier 10. A specimen instillation port 12 exposed outside the cover 20 is formed on one side of the specimen holding area 11, and an air channel 13 extending beyond the other side of the cover 20 is selectively formed on the other side of the specimen holding area 11. The air channel 13 may prevent air filling the inside of the specimen holding area 11 causing instillation unable to be performed when the specimen is a fluid. In addition, the specimen instillation port 12 of the present embodiment is designed to have a shape expanding outwards, which may lower the possibility of the specimen unable to be smoothly instilled.

Figure 2:
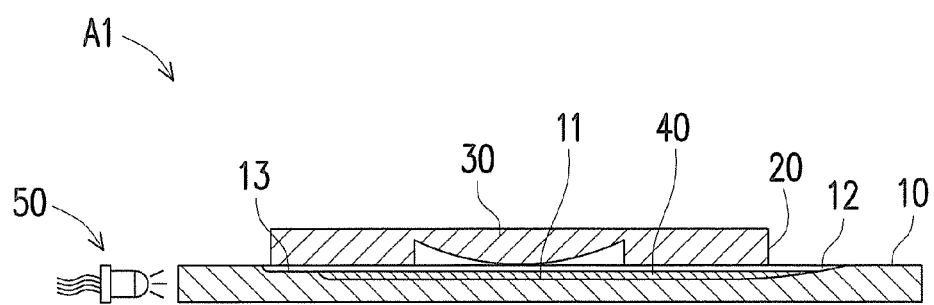
FIG. 2 is a cross-sectional view of the testing equipment of FIG. 1A.

As shown in FIG. 2, a lateral illumination device 50 may be selectively disposed at one side of the carrier. Mainly, the brightness of the specimen 40 in the specimen holding area 11 may be increased by the addition of the lateral illumination device 50 to obtain better testing resolution.

Figure 3:
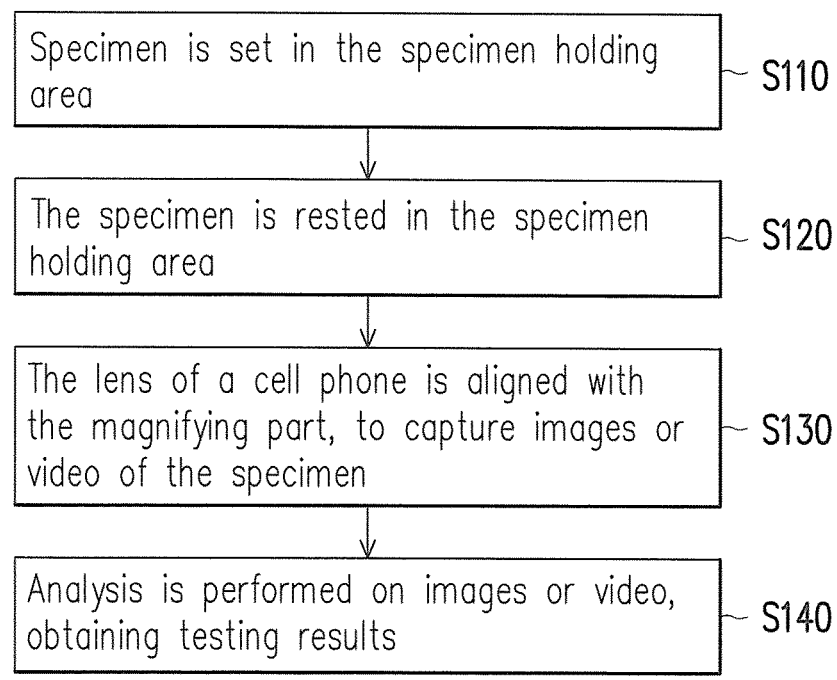
FIG. 3 is a flow diagram of testing for a testing equipment according to an embodiment of the invention.

When using the testing equipment A1 with magnifying function shown in FIG. 1B for performing testing, first the specimen 40 desired to be tested is set in the specimen holding area 11 (labelled in FIG. 1A), this is step S110 shown in FIG. 3. In step S110, the cover 20 may first be stacked on top the carrier 10, before setting the specimen 40 desired to be tested in the specimen holding area 11 from the specimen instillation port 12. Of course, the specimen 40 desired to be tested may be set in the specimen holding area 11 directly first, and then stacking the cover 20 on top the carrier 10. Next, the specimen 40 is rested in the specimen holding area 11 selectively for a period of time according to testing requirements of the specimen 40, this is step S120 shown in FIG. 3. Later, a cell phone is attached on the cover 20, and the camera of the cell phone is aligned with the magnifying part 30, to conveniently use the camera of the cell phone to capture a picture or video of the specimen through the magnifying part 30, this is step S130 shown in FIG. 3. Lastly, an application (APP) installed in the cell phone or other analysis device may be used to perform analysis of the picture or video, for obtain testing results, this is step S140 shown in FIG. 3.

Figure 4:
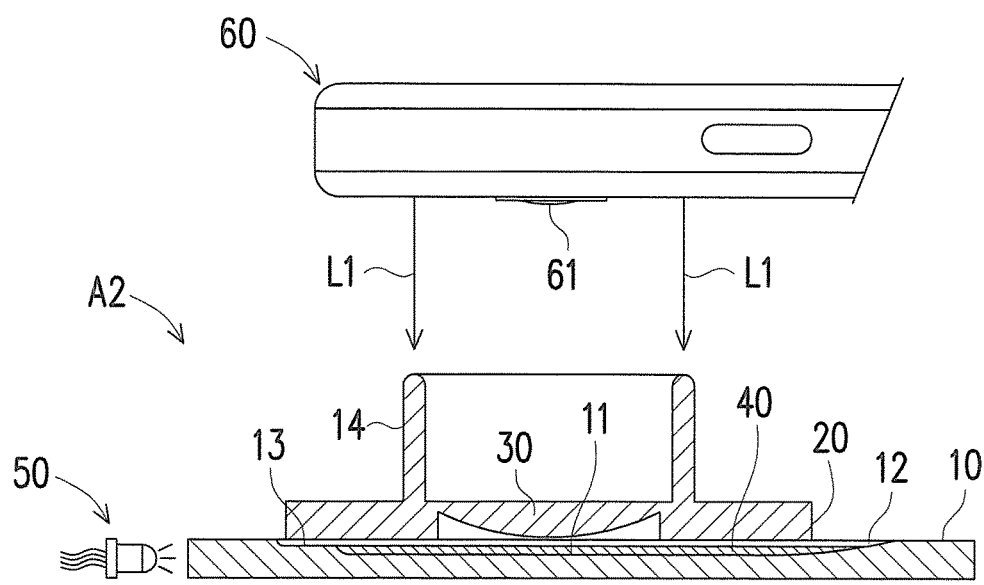
FIG. 4 is a cross-sectional view of a testing equipment with magnifying function according to another embodiment of the invention.

As shown in FIG. 4, a supporting side (such as a protruding part) 14 may further be formed on a top of the cover 20 of a testing equipment A2 at a periphery of the magnifying part 30. In the present embodiment, a protruding type support structure may be formed on top of the cover 20 by the addition of the protruding part 14. When the user desires to adopt an existing intelligent communications device 60 to perform testing, a side of the intelligent communications device 60 having a camera 61 disposed may be abutted on the protruding part 14 (along the direction shown by the arrow L1), to achieve a stable supporting function and effect. In this way, the testing equipment A2 of the present embodiment may allow the user to arrange the intelligent communications device 60 for performing testing, and does not require an expensive testing apparatus for obtaining testing records of pictures and even recordings. Furthermore, regarding the design dimensions of the protruding part 14, considerations regarding the best observation distance for the user may be made in advance, enhancing the ease of use.

Figure 5:
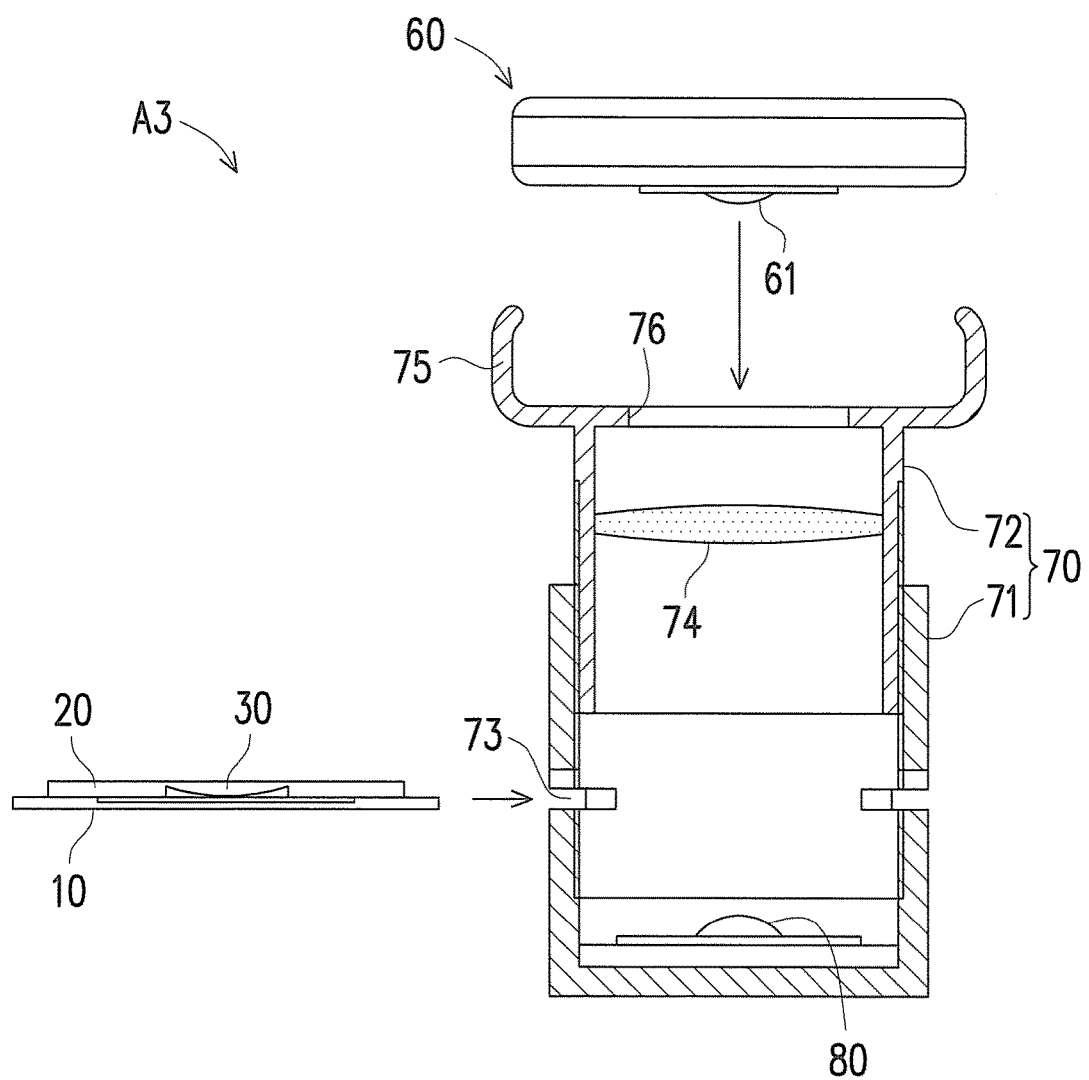
FIG. 5 is a cross-sectional view of a testing equipment with magnifying function according to another embodiment of the invention.
Figure 6:
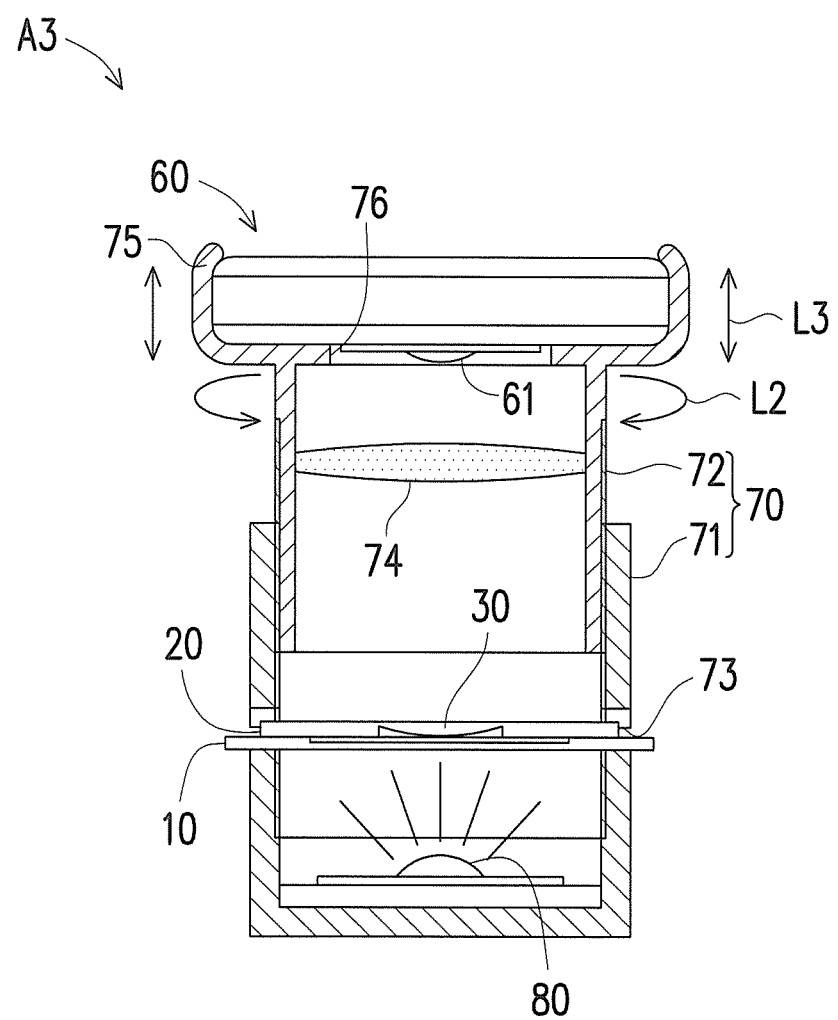
FIG. 6 is a schematic diagram of the testing equipment of FIG. 5 in a usage state.

As shown in FIG. 5 and FIG. 6, a testing equipment A3 of the present embodiment may include a barrel type base 70. The barrel type base 70 includes a lower barrel base 71 and a liftable-descendable upper barrel body 72. The lower barrel base 71 has a lateral insertion port 73 providing an insert position for the cover 20 and the carrier 10 in a stacked state. An upward lighting device 80 is disposed on a bottom part of the lower barrel base 71, to address the space below the cover 20 and the carrier 10. That is to say, lighting may be provided to the cover 20 and the carrier 10. At least one magnification lens 74 is disposed in the upper barrel body 72. The upper barrel body 72 is rendered in a screw configuration with respect to the lower barrel base 71 and may be lifted and descended like a screw. Namely, the upper barrel body 72 is rotated with respect to the lower barrel base 71 along the arrow L2 directions for the upper barrel body 72 to move along the arrow L3 directions with respect to the lower barrel base 71, to adjust the height position of the magnification lens 74, further achieving an objective of adjusting the magnification. An assembling frame 75 may be disposed at an upper end of the upper barrel body 72. The assembling frame 75 may provide the existing intelligent communications device 60 with assembly positioning. The assembling frame 75 has a camera alignment hole 76. The camera alignment hole 76 is provided to be used to correspond with the camera 61 of the intelligent communications device 60. The testing equipment A3 disclosed in the present embodiment may achieve a more complete and better to use magnifying testing function.

The camera 61 disposed on current intelligent communications device 60 typically only have a digital zoom function. If higher accuracy testing is performed, generally an optical zoom lens is additionally required. However, the user using an arrangement of the testing equipment A3 and the intelligent communications device 60 of the present embodiment, does not require an optical zoom lens to be additionally prepared, and furthermore the trouble of perfectly aligning the three, the intelligent communications device 60, the optical zoom lens and the specimen is saved. Furthermore, by arranging with the original digital zoom function of the camera 61, even more accurate testing may be performed.

FIG. 6 shows the intelligent communications device 60 in a state already assembled and positioned on the assembling frame 75 which is disposed on the upper barrel body 72. Housed is the specimen 40, and the cover 20 and the carrier 10 in a stacked state are at the insert position in the lateral insertion port 73. The upward lighting device 80 may increase the brightness of the specimen. Then, the upper barrel body 72 or the barrel type base 70 is rotated as shown in arrow L2 of FIG. 6, to liftably-descendably adjust the height position of the magnification lens 74 along the direction indicated by the arrow L3 of FIG. 6. In this way, a function of adjusting the magnification may be achieved. The user may capture dynamic or static testing images of the specimen 40 after magnification through the camera 61 disposed on the intelligent communications device 60. Furthermore, the originally equipped functions of the intelligent communications device 60 may be used directly to perform storage and transferring of the testing images and such subsequent processes.

Figure 7:
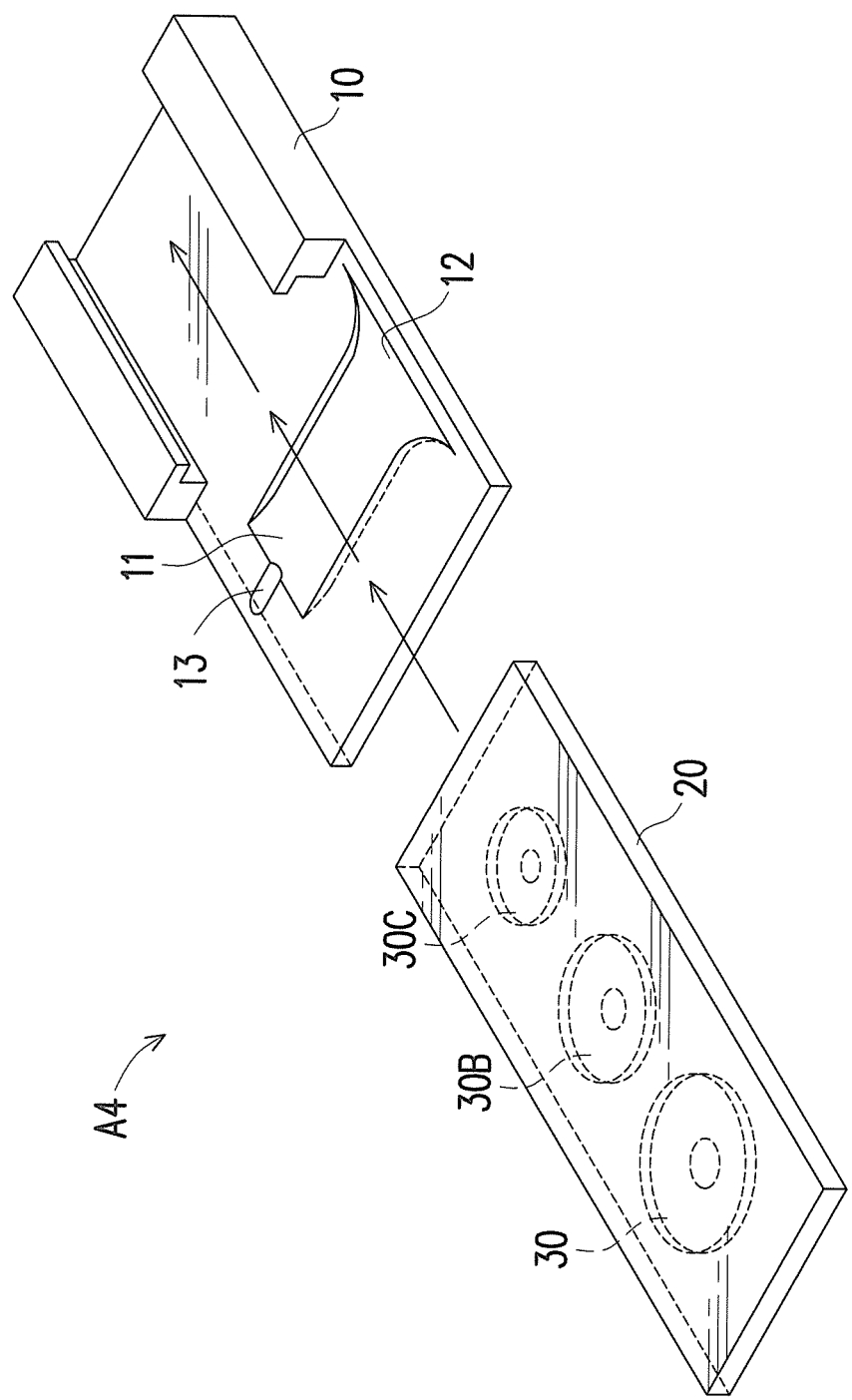
FIG. 7 is a schematic diagram of a testing equipment with magnifying function according to another embodiment of the invention.

As shown in FIG. 7, a testing equipment A4 with magnifying function includes a plurality of magnifying parts 30, 30B, 30C of different magnifications disposed in intervals on the cover 20. The user may shift the cover 20 to align the specimen holding area 11 of the carrier 10 with any of the magnifying parts 30, 30B, 30C of different magnifications, conveniently obtaining testing results with different magnifications. By this design, the testing equipment A4 with magnifying function of a single module may satisfy the different needs of the user, saving the trouble of changing the magnifying part.

Figure 8:
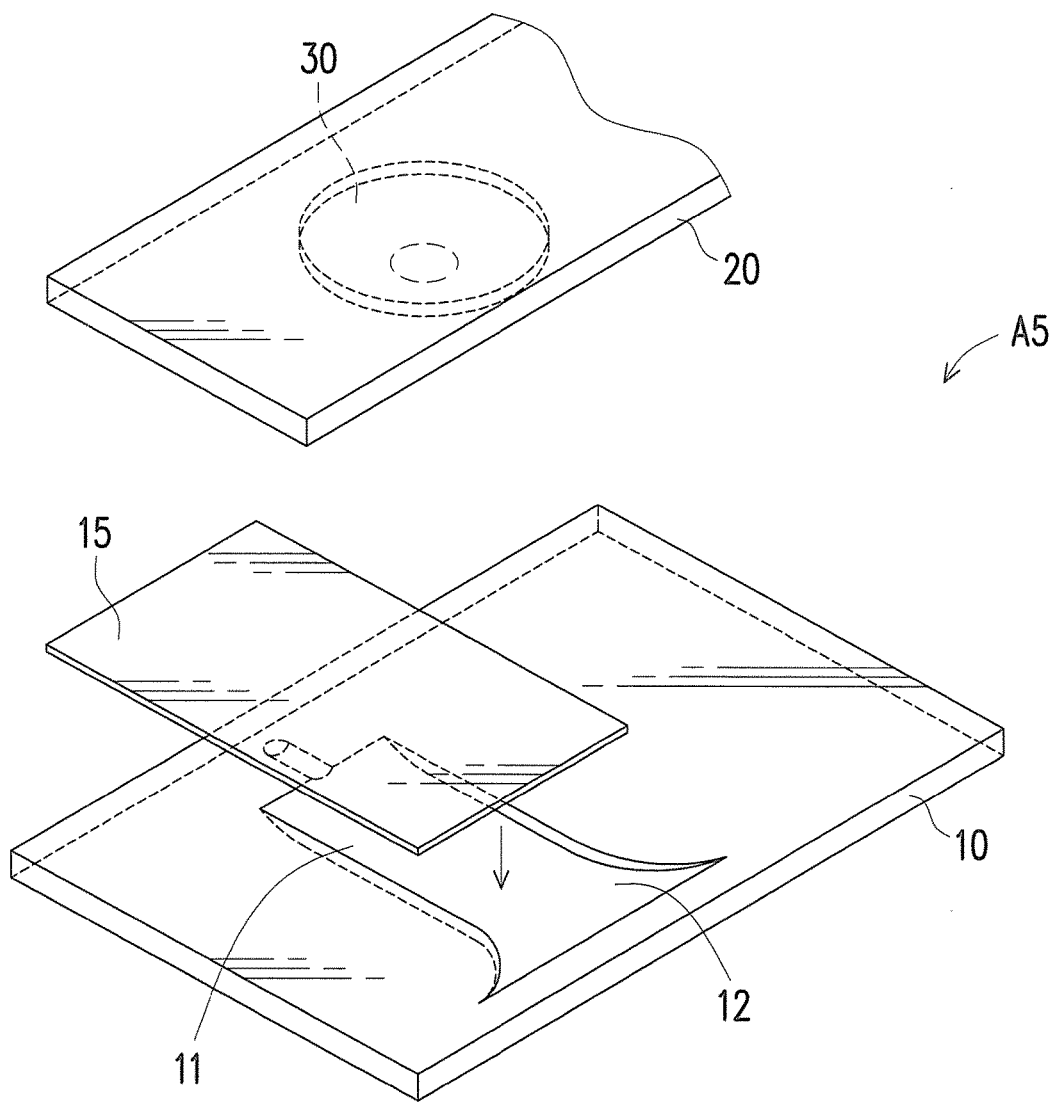
FIG. 8 is a schematic diagram of a testing equipment with magnifying function according to another embodiment of the invention.

As shown in FIG. 8, a testing equipment A5 with magnifying function of the present invention further includes a flexible transparent film 15. The flexible transparent film 15 is disposed between the carrier 10 and the magnifying part 30, and is covered on the specimen holding area 11. The flexible transparent film 15 covers the specimen 40 (liquid) such that it tends to be in a confined steady state, such that outside air, dust and dirt interference factors are kept to the lowest. Furthermore, the testing equipment A5 may adjust the focal length by the thickness of the flexible transparent film 15.

Figure 9:
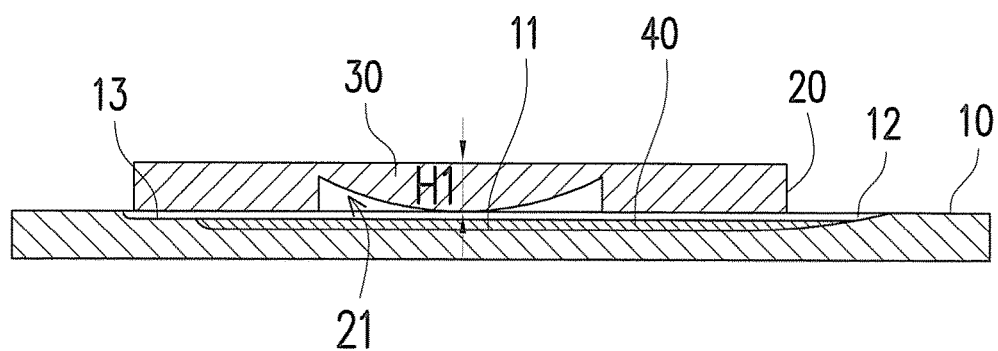
FIG. 9 is a schematic diagram of a testing equipment with magnifying function according to another embodiment of the invention.
Figure 10:
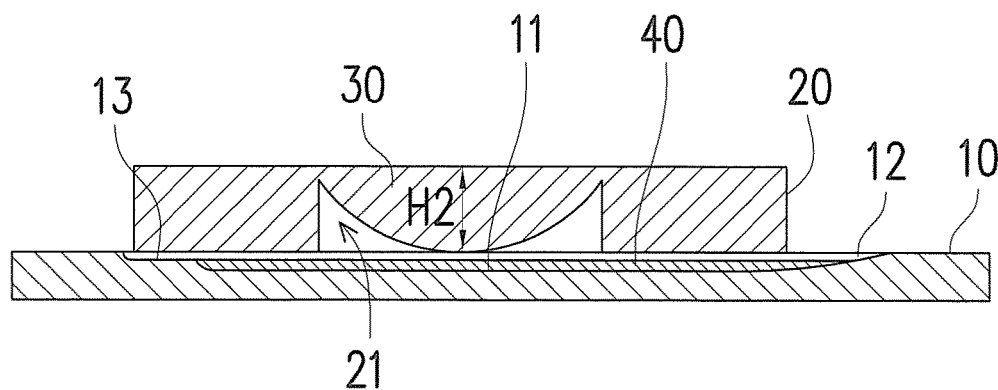
FIG. 10 is a schematic diagram of a testing equipment with magnifying function according to another embodiment of the invention.

As shown in FIG. 9, the magnifying part 30 of a testing equipment A6 with magnifying function is a planar convex lens, and a surface of the magnifying part 30 facing the carrier 10 is a protruding surface. Therefore, an upwardly concave type hollow part 21 is formed at the surface of the magnifying part 30 facing the carrier 10. A focal length parameter H1 is defined by the thickness of the thickest part of the magnifying part 30 of the planar convex lens. As shown in FIG. 10, a focal length parameter H2 of a testing equipment A7 with magnifying function is different than the focal length parameter H1 of FIG. 9.

The focal lengths H1 and H2 may change by the change in thickness of the cover 20 or the size of the curvature of the magnifying part 30 or differences in the change of thickness. The focal length H2 as shown in FIG. 10 is greater than the focal length H1 shown in FIG. 9, and is achieved by changing the size of the curvature of the magnifying part 30. In this way, testing requirements with different focal lengths may be satisfied through the changing of different magnifying parts 30.

The magnifying part 30 may be the only part rendered a transparent state and the cover 20 is a matte state. In addition, the carrier 10 may have only the specimen holding area 11 rendered in a transparent state, and the remaining parts then may be a matte state. In this way, when the testing operations are performed on the testing equipment, the translucent bright area may be concentrated at the specimen holding area 11, the magnifying part 30 and such main observation parts, lowering the light beam interference phenomenon from other parts.

Figure 11:
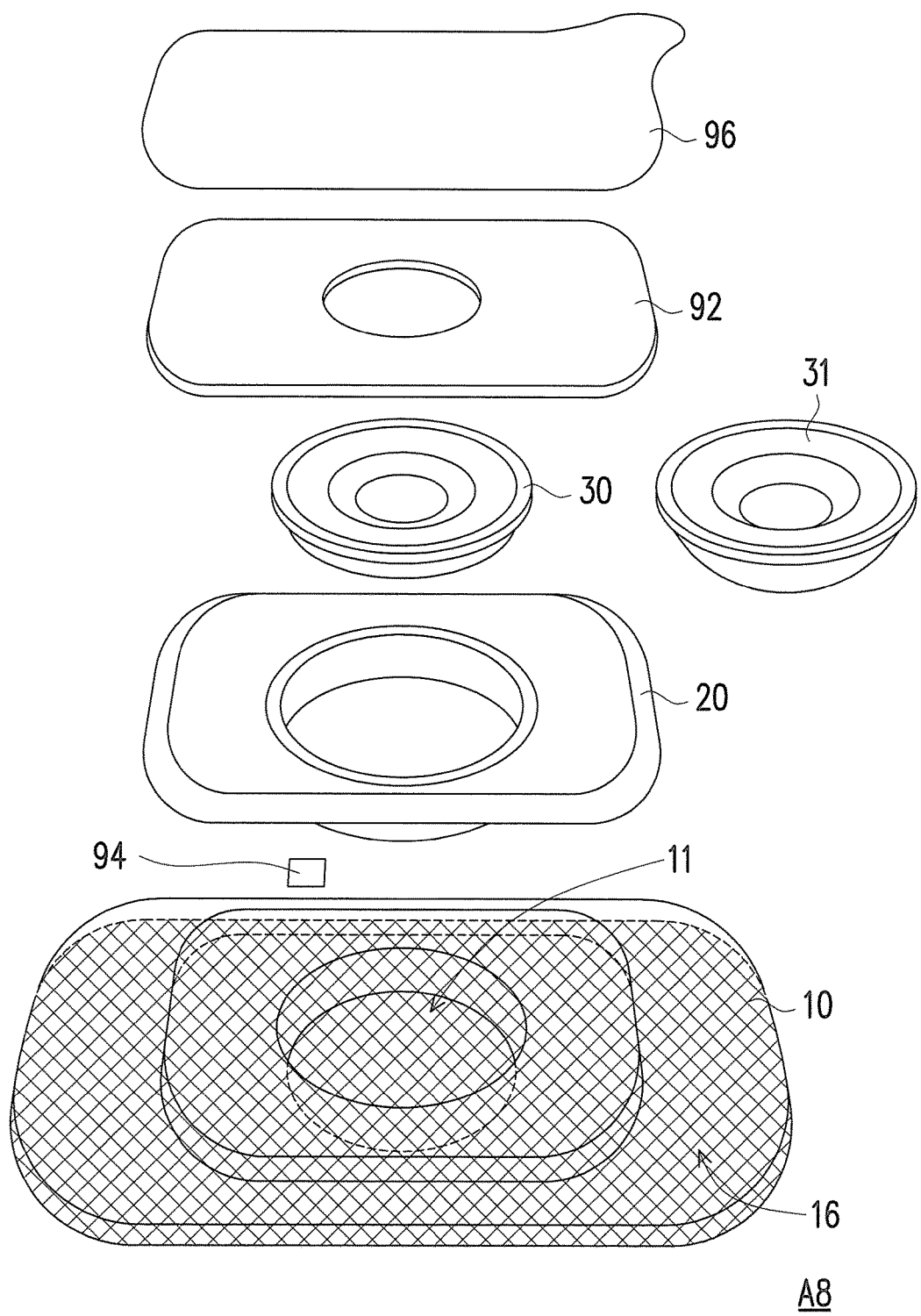
FIG. 11, FIG. 12 and FIG. 13 are exploded views of testing equipments with magnifying function according to another three embodiments of the invention.

Next referring to FIG. 11, in a testing equipment A8 with magnifying function of the present embodiment, the carrier 10 of the testing equipment A8 further has a light beam auxiliary guiding structure 16 formed at the bottom surface of the carrier 10. A material of the carrier 10 is made from transparent or translucent material. For example, the light beam auxiliary guiding structure 16 may be a matte structure, a granular structure, a rough pattern, an engraved pattern, or other suitable structure that scatters the arriving light beam, and the light beam auxiliary guiding structure 16 may be an entire surface or constitute a particular pattern. Of course, the light beam auxiliary guiding structure 16 may also be formed all around the side surfaces of the carrier 10. When the cover 20 and the carrier 10 in a stacked state are attached to the intelligent communications device 60 (refer to FIG. 4), the magnifying part 30 corresponds with the camera 61 of the intelligent communications device 60. In addition, a fill light (not shown) is disposed near the camera 61 on parts of the intelligent communications device 60. The light beam provided by the fill light may be guided in the carrier 10 to illuminate the specimen holding area 11 through the cover 20. At the same time, the light beam auxiliary guiding structure 16 of the carrier 10 may cause the light beam provided by the fill light to scatter, further increasing the brightness of the specimen holding area 11. By disposing the light beam auxiliary guiding structure 16, the testing equipment does not require an additional fill light source to illuminate the carrier 10, achieving an objective of illuminating the specimen. In the present embodiment, the cover 20 correspondingly covers the fill light of the intelligent communications device 60 as an example. Therefore, a light transmissible material is required to be adopted for the cover 20. However, the cover 20 may also not cover the fill light, in which the light beam provided by the fill light directly illuminates the carrier 10.

The testing equipment A8 with magnifying function of the present embodiment may selectively include a non-slip film 92 and a pH test paper 94. The non slip film 92 is attached on the supporting side (such as the top) of the cover 20, and is used to stably position the cover 20 to the camera 61 of the intelligent communications device 60, as shown in FIG. 4, such that the magnifying part 30 corresponds with the camera 61 of the intelligent communications device 60, composing the positioning of the intelligent communications device 60 on the testing equipment A8 and making the positioning state of the intelligent communications device 60 with the testing equipment A8 better through the disposition of the non slip film 92. The non slip film 92 of the present embodiment has an opening corresponding to the magnifying part 30, to prevent interference with the user observing the specimen through the magnifying part 30; however it should not be construed as a limitation to the invention. A material of the main body of the non slip film 92, for example, is silicon. Due to disposing the non slip film 92, release paper may be used to protect the surface of the non slip film 92, to maintain adhesion. In addition, the pH test paper 94 may be disposed on the specimen holding area 11 of the carrier 10, to provide a function for measuring the pH value of the specimen. Of course, the pH test paper 94 may be replaced after use.

In addition, the magnifying part 30 and the cover 20 in the present embodiment adopts a separable type design. Therefore, the user may select a magnifying part 31 different from the magnifying part 30 to replace the original magnifying part 30 according to testing requirements. The magnifying part 31 and the cover 20 are assembled to obtain different magnifications or other optical features.

Figure 12:
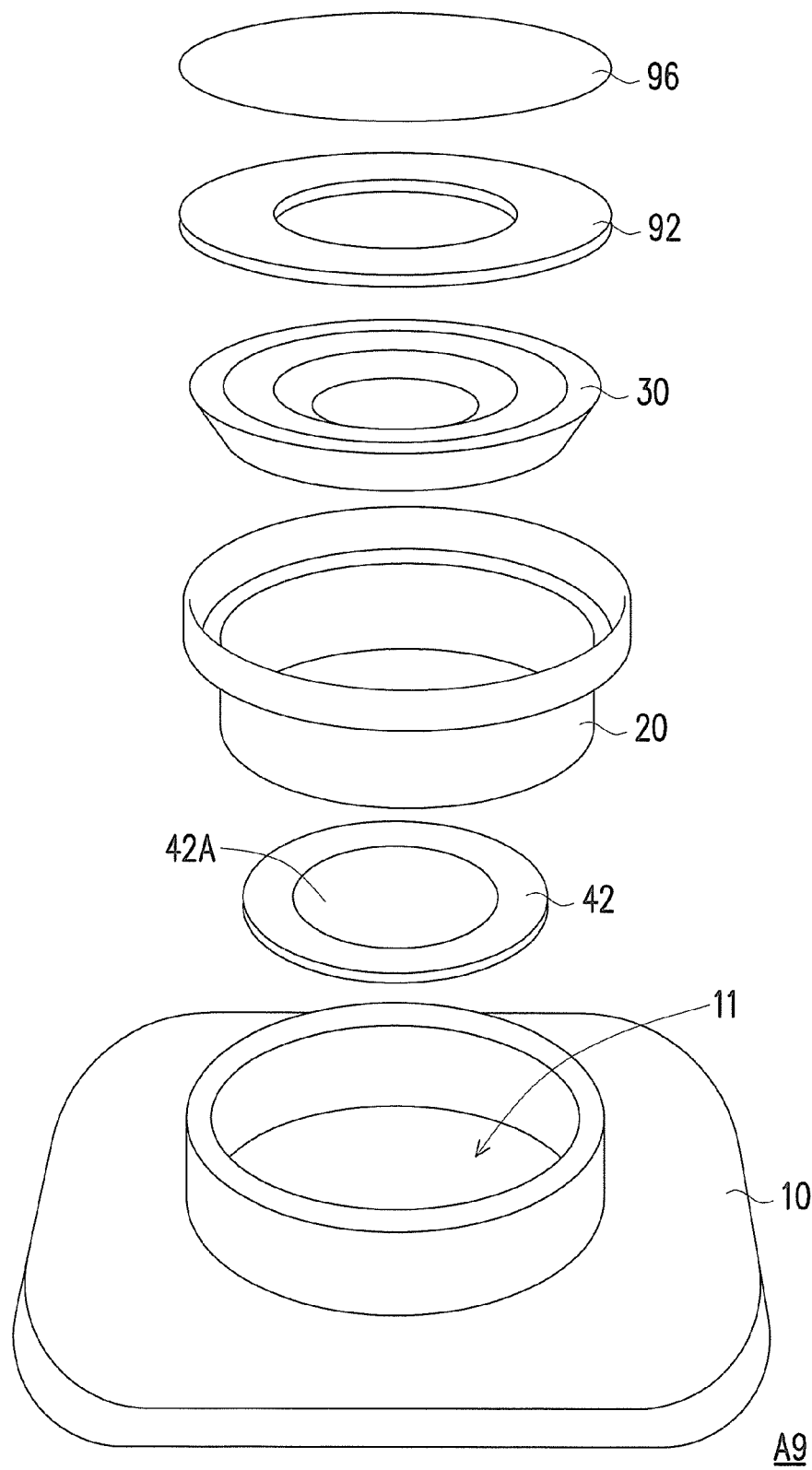

Next, referring to FIG. 12, a testing equipment A9 with magnifying function of the present embodiment further includes a specimen collection sheet 42 disposed in the specimen holding area 11. The specimen collection sheet 42, for example, has a specimen collection area 42A, using adhesion or other methods to collect subcutaneous tissue/cells, parasite eggs and the like solid test bodies.

Figure 13:
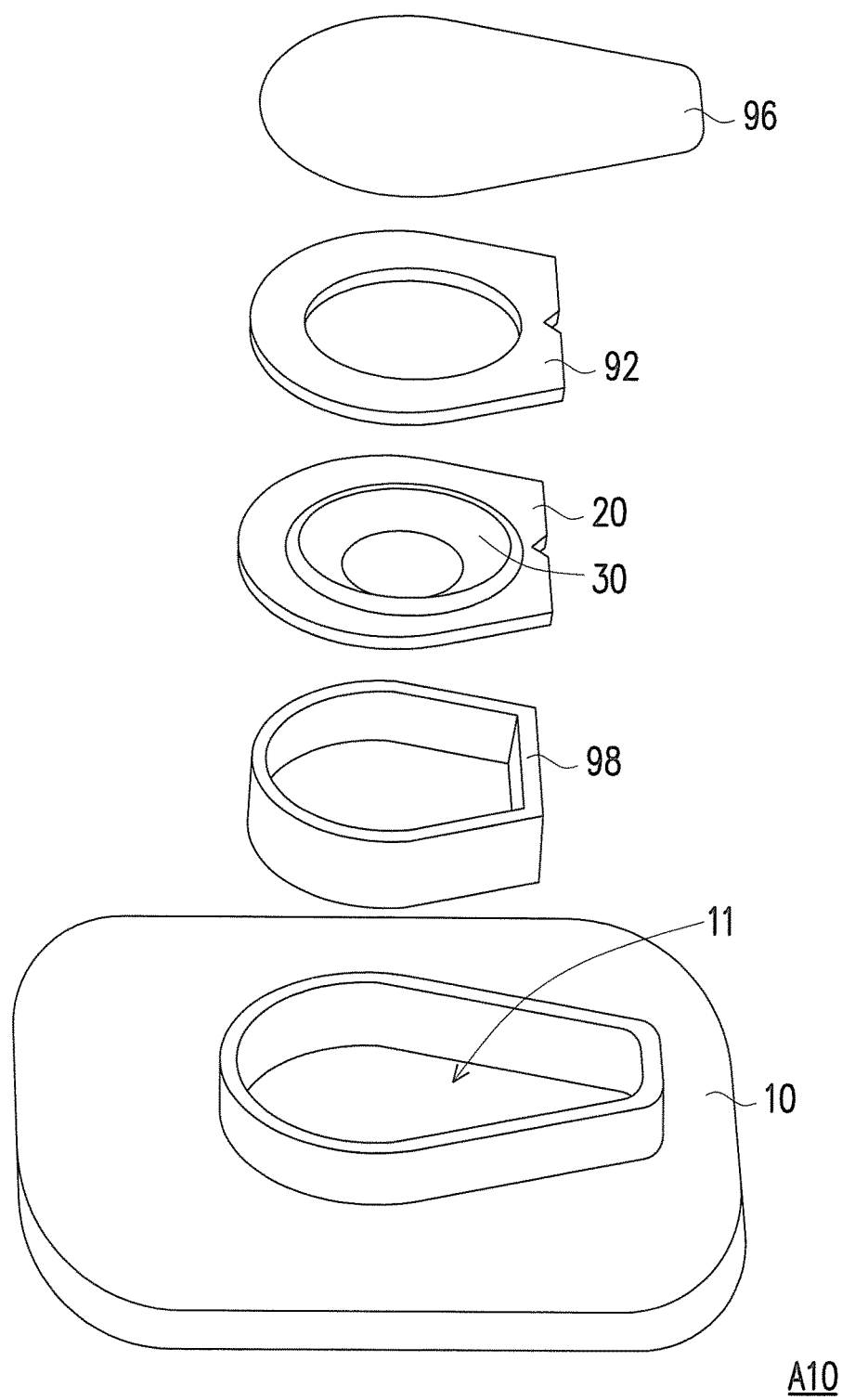

Next, referring to FIG. 13, a testing equipment A10 with magnifying function further includes an isolation component 98 disposed at the specimen holding area 11 between the carrier 10 and the cover 20. The isolation component 98 may isolate the magnifying part 30 and the testing fluid in the specimen holding area 11, preventing the testing fluid contaminating the magnifying part 30.

In summary, the testing equipment with magnifying function of the invention makes the conventional structures mentioned in the "Prior Art" of the invention capable of providing a simple structure significantly lowering the cost of the simple specimen magnifying testing structure, such as sperm test or urinalysis, and further satisfying requirements for achieving diverse usages, mainly through the carrier having the specimen holding area, the magnifying part and such unique innovative type structures and technical features. The testing equipment with magnifying function of the invention also can be applied to inspect the counts, the motility and the morphology of the specimen. The testing equipment with magnifying function of the invention is suitable for at-home-test; the results of the test can be obtained very quickly and inexpensive. The testing equipment with magnifying function of the invention provides a way to assess male fertility at home for couples seeking pregnancy to determine which further medical intervention is needed. Furthermore, it may be conveniently integrated with existing intelligent communications device, and enables the use of existing intelligent communications device to capture magnified testing images and perform subsequent operations such as storing and transferring, achieving improvements for more complete and better to use testing functions.

On the other hand, by disposing of the light beam auxiliary guiding structure the testing equipment does not require an additional light source to illuminate the carrier, achieving an objective of illuminating the specimen, further enhancing testing results. At the same time the testing equipment with magnifying function has the feature of low cost, and therefore may achieve an objective of disposable use. Of course, the testing equipment with magnifying function of the invention may be reused.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A testing equipment with magnifying function, comprising:
    a carrier made of a transparent or translucent material, having at least one specimen holding area and a rough pattern or an engraved pattern;
    a detachable cover, at least stacked on the specimen holding area of the carrier;
    at least one magnifying part, integrally formed at the detachable cover, the magnifying part is disposed to align with the specimen holding area of the carrier; and
    a lateral illuminator disposed on a side of the carrier for providing illumination to the specimen holding area through the carrier, wherein the carrier guides light beams from the lateral illuminator through the transparent or translucent material, and the rough pattern or the engraved pattern of the carrier reflects the light beams to illuminate the specimen holding area.

2. The testing equipment with magnifying function as claimed in claim 1, wherein a plurality of magnifying parts are disposed in intervals at the detachable cover, each of the magnifying parts having a different magnification ratio.

3. A system for testing a biological specimen, comprising:
    a testing equipment with magnifying function of claim 1;
    a base component including:
        an insertion port for inserting the testing equipment of claim 1 into the base component; and
        a camera component for capturing the image of the specimen holding area, or a form-fitting frame for securing a mobile device that includes a camera component for capturing the image of the specimen holding area.

4. The system of claim 3, wherein the base component further includes:
    a light source for providing illumination to the specimen holding area.

5. The system of claim 4, wherein the base component further includes:
    a light collimator for collimating light beams emitted from the light source to the specimen holding area.

6. The system of claim 5, wherein the base component further includes:
    an annular diaphragm between the light source and the light collimator for forming a hollow cone of light beams that travels through the light collimator and then reaches the specimen holding area.

7. The system of claim 3, wherein the base component includes a lower barrel base and an upper barrel body, the upper barrel body is rendered in a screw configuration with respect to the lower barrel base such that the upper barrel body can be lifted or descended by rotating the upper barrel body with respect to the lower barrel base.

8. The system of claim 7, wherein the upper barrel body includes a magnification lens, and a height position of the magnification lens is adjustable by lifting or descending the upper barrel body for dynamically adjusting magnification.

9. The system of claim 3, wherein when the mobile device is secured by the form-fitting frame, and a lens of the camera component of the mobile device is aligned with the magnifying part and the specimen holding area.

10. The testing equipment with magnifying function of claim 1, wherein the carrier includes a specimen installation port exposed outside the detachable cover for retrieving a specimen onto the specimen holding area.

11. The testing equipment with magnifying function of claim 1, further comprising:
a pH test component disposed on the specimen holding area for measuring pH value of a specimen.

12. A testing equipment with magnifying function, comprising:
a carrier made of a transparent or translucent material, having at least one specimen holding area on top and a rough pattern or an engraved pattern, and having a light beam auxiliary guiding structure, wherein the light beam auxiliary guiding structure guides a light beam of an outside environment to the specimen holding area of the carrier;
a detachable cover, at least stacked on the specimen holding area of the carrier, and the detachable cover having a supporting side for an intelligent communications device;
at least one magnifying part, integrally formed at the detachable cover, the magnifying part is disposed to align with the specimen holding area of the carrier; and
a lateral illuminator disposed on a side of the carrier for providing illumination to the specimen holding area through the carrier, wherein the carrier guides light beams from the lateral illuminator through the transparent or translucent material, and the rough pattern or the engraved pattern of the carrier reflects the light beams to illuminate the specimen holding area.

13. The testing equipment with magnifying function as claimed in claim 12, further comprising:
a nonslip film, attached at the supporting side for the intelligent communications device of the detachable cover, and used to attach the detachable cover to a camera of the intelligent communications device, so the magnifying part corresponds to the camera of the intelligent communications device.

* * * * *